US008178117B2

(12) United States Patent
Taranta et al.

(10) Patent No.: US 8,178,117 B2
(45) Date of Patent: May 15, 2012

(54) LIQUID WATER BASED AGROCHEMICAL FORMULATIONS

(75) Inventors: Claude Taranta, Stutensee (DE);
Wolfgang Meier, Limburgerhof (DE);
Karl Strauss, Limburgerhof (DE);
Arnold Kraushaar, Sinsheim (DE);
Ulrich Steinbrenner, Neustadt (DE)

(73) Assignee: BASF SE, Ludwigshafen (DE)

( * ) Notice: Subject to any disclaimer, the term of this patent is extended or adjusted under 35 U.S.C. 154(b) by 269 days.

(21) Appl. No.: 12/515,749

(22) PCT Filed: Nov. 9, 2007

(86) PCT No.: PCT/EP2007/062110
§ 371 (c)(1),
(2), (4) Date: May 21, 2009

(87) PCT Pub. No.: WO2008/061899
PCT Pub. Date: May 29, 2008

(65) Prior Publication Data
US 2010/0016155 A1  Jan. 21, 2010

(30) Foreign Application Priority Data
Nov. 22, 2006 (EP) ..................... 06124554

(51) Int. Cl.
*A01N 25/00* (2006.01)
*A01N 43/56* (2006.01)
*A01N 31/08* (2006.01)
*A61K 31/05* (2006.01)

(52) U.S. Cl. .......... 424/405; 514/731; 514/736
(58) Field of Classification Search .......... None
See application file for complete search history.

(56) References Cited

U.S. PATENT DOCUMENTS

| | | | |
|---|---|---|---|
| 3,666,785 A | 5/1972 | Sakai et al. | |
| 4,272,920 A * | 6/1981 | Dawson | 47/58.1 R |
| 4,283,222 A | 8/1981 | Horide et al. | |
| 4,541,860 A | 9/1985 | Civilla et al. | |
| 4,945,100 A | 7/1990 | Nyfeler et al. | |
| 4,973,352 A | 11/1990 | Heinrich et al. | |
| 5,045,311 A | 9/1991 | Pinter et al. | |
| 5,192,793 A | 3/1993 | Szekely et al. | |
| 5,334,585 A | 8/1994 | Derian et al. | |
| 5,911,915 A | 6/1999 | Fonsny et al. | |
| 6,455,471 B1 * | 9/2002 | Gubelmann-Bonneau et al. | 504/133 |
| 6,494,082 B1 | 12/2002 | Mizobe | |
| 6,602,823 B1 | 8/2003 | Röchling et al. | |
| 6,664,213 B1 | 12/2003 | Furusawa et al. | |
| 6,737,553 B1 | 5/2004 | Maas et al. | |
| 7,256,317 B2 | 8/2007 | Maas et al. | |
| 2004/0157745 A1 | 8/2004 | Vermeer et al. | |
| 2007/0066489 A1 | 3/2007 | Vermeer et al. | |
| 2008/0153706 A1 | 6/2008 | Frisch et al. | |
| 2008/0214683 A1 | 9/2008 | Steinbrenner et al. | |
| 2010/0137375 A1 | 6/2010 | Finch | |
| 2010/0210461 A1 | 8/2010 | Stoesser et al. | |
| 2010/0227763 A1 | 9/2010 | Krapp et al. | |
| 2010/0234457 A1 | 9/2010 | Taranta et al. | |
| 2011/0039698 A1 | 2/2011 | Taranta et al. | |
| 2011/0105333 A1 | 5/2011 | Israels et al. | |
| 2011/0124590 A1 | 5/2011 | Sowa et al. | |

FOREIGN PATENT DOCUMENTS

| | | |
|---|---|---|
| CA | 2 068 826 | 11/1992 |
| CA | 1 334 274 | 2/1995 |
| DE | 69012487 | 2/1995 |
| DE | 198 57 963 | 6/2000 |
| EP | 0126430 | 11/1984 |
| EP | 0160182 | 11/1985 |
| EP | 0330904 | 9/1989 |
| EP | 0 341 126 | 11/1989 |
| EP | 0 514 769 | 11/1992 |
| EP | 0728414 | 8/1996 |
| EP | 1 140 741 | 10/2001 |
| EP | 1339281 | 6/2002 |
| EP | 1702607 | 9/2006 |
| FR | 2609631 | 7/1988 |
| RU | 2238649 | 10/2004 |
| WO | WO 90/06681 | 6/1990 |
| WO | WO 90/09103 | 8/1990 |
| WO | WO 96/01305 | 1/1996 |
| WO | WO 99/66300 | 12/1999 |
| WO | WO 00/35278 | 6/2000 |
| WO | WO 00/78139 | 12/2000 |
| WO | WO 02/42488 | 5/2002 |

(Continued)

OTHER PUBLICATIONS

International Search Report completed Jan. 14, 2009, in International Application No. PCT/EP2007/062110, filed Nov. 9, 2007.
Mulqueen, Patrick, J., et al., "Recent Developments in Suspoemulsions", Pestic. Sci., 1990, p. 451-465, vol. 29.
International Preliminary Report on Patentability dated May 26, 2009, from corresponding International Application No. PCT/EP2007/062110, filed Nov. 9, 2007.
Karakotov et al., "Tebuconazole-Based Fungicidal Composition," Shchelkovo Agrokhim Stock Chem., Jun. 19, 2003, XP002498611.
Rhee et al., "Formulation of Parenteral Microemulsion Containing Itraconazole," Arch. Pharm. Res., vol. 30, No. 1, 2007, pp. 114-123.
Shell Chemicals, "Methyl Proxitol Acetate," Mar. 16, 2007, XP007914204.
Skelton et al., "Formulation of Pesticide Microemulsions," Pesticide Formulations and Application Systems, vol. 8, 1988, pp. 36-45, XP002053622.
Tomšič et al., "Ternary Systems of Nonionic Surfactant Brij 35, Water and Various Simple Alcohols: Structural Investigations by Small-Angle X-ray Scattering and Dynamic Light Scattering," Journal of Colloid and Interface Science, vol. 294, 2006, pp. 194-211.

*Primary Examiner* — Ernst Arnold
(74) *Attorney, Agent, or Firm* — Brinks Hofer Gilson & Lione

(57) ABSTRACT

The present invention relates to a formulation comprising (a) at least one pesticide; and (b) at least one non-ionic surfactant of formula (I): $R^1$—O-$(AO)_x$—(H); wherein $R^1$ represents straight-chain or branched alkyl having 4 to 20 carbon atoms; AO is ethyleneoxy, propyleneoxy or a mixture of ethyleneoxy and propyleneoxy; and x correspond to values from 2 to 30; and (c) at least one ionic tristyrylphenyl alkoylate; and (d) at least one oil; and (e) water, wherein the pesticide is present in the aqueous phase in form of a suspension and the oil is essentially free of pesticide.

13 Claims, No Drawings

FOREIGN PATENT DOCUMENTS

| | | |
|---|---|---|
| WO | WO 02/43488 | 6/2002 |
| WO | WO 03/000053 | 1/2003 |
| WO | WO 03/022049 | 3/2003 |
| WO | WO 2005/105285 | 11/2005 |
| WO | WO 2006/030006 | 3/2006 |
| WO | WO 2006/114186 | 11/2006 |
| WO | WO 2007/017501 | 2/2007 |
| WO | WO 2007/057028 | 5/2007 |
| WO | WO 2007/110355 | 10/2007 |
| WO | WO 2008/043807 | 4/2008 |
| WO | WO 2009/019299 | 2/2009 |
| WO | WO 2009/133166 | 11/2009 |
| WO | WO 2010/010005 | 1/2010 |

\* cited by examiner

LIQUID WATER BASED AGROCHEMICAL FORMULATIONS

This application is a National Stage application of International Application No. PCT/EP2007/062110 filed Nov. 9, 2007, the entire contents of which is hereby incorporated herein by reference. This application also claims the benefit under 35 U.S.C. §119 of European Patent Application No. 06124554.4, filed Nov. 22, 2006, the entire contents of which is hereby incorporated herein by reference.

The present invention relates to a formulation comprising
(a) at least one pesticide; and
(b) at least one non-ionic surfactant of formula I $$R^1\text{—}O\text{-}(AO)_x\text{—}(H) \qquad (I)$$

wherein
$R^1$ represents straight-chain or branched alkyl having 4 to 20 carbon atoms;
AO is ethyleneoxy, propyleneoxy or a mixture of ethyleneoxy and propyleneoxy; and
x correspond to values from 2 to 30; and
(c) at least one ionic tristyrylphenyl alkoylate; and
(d) at least one oil; and
(e) water,
wherein the pesticide is present in the aqueous phase in form of a suspension and the oil is essentially free of pesticide.

Agricultural formulations comprising alkoxylated tristyrylphenoles are known. WO 2006/114186 discloses water in oil suspoemulsions, wherein the oil phase comprises the pesticide. EP 0514769 discloses suspoemulsions comprising a herbicide, an aromatic solvent and ethoxylated tristyrylphenoles. The term suspoemulsions is defined therein according to Mulqeen et al., Pesticide Science, 1990, 29, 451-465 as combination of "an emulsion phase, containing one or more active ingredients, with a continuous phase also containing one of more active ingredients in the form of a solid dispersion." U.S. Pat. No. 6,664,213 B1 discloses a liquid pesticide composition comprising a pesticidally active ingredient and a polyoxaethylene alkyl ether which has a HLB value of 6 to 13.5 and a content of 10 to 50 wt % based on the composition. WO 00/78139 discloses a liquid herbicide composition containing carfentrazone-ethyl- an anionic surfactant, a water-soluble organic compound and water and having a pH of from 2 to 7.

On of the object the formulation chemist is faced with is to develop formulations, in which actives are kept in stable suspension. Another object is that it is desirable for many applications in plant protection to provide a formulation, which is capable of keeping more than one active dispersed, or which is capable of keeping a couple of actives in suspension and at least one oil emulsified in the same medium.

The object was solved by a formulation comprising
(a) at least one pesticide;
(b) at least one non-ionic surfactant of formula I $$R^1\text{—}O\text{-}(AO)_x\text{—}(H) \qquad (I)$$

wherein
$R^1$ represents straight-chain or branched alkyl having 4 to 20 carbon atoms;
AO is ethyleneoxy, propyleneoxy or a mixture of ethyleneoxy and propyleneoxy; and
x correspond to values from 2 to 20; and
(c) at least one ionic tristyrylphenyl alkoylate; and
(d) at least one oil; and
(e) water,
wherein the pesticide is present in the aqueous phase in form of a suspension and the oil is essentially free of pesticide.

The formulation may also optionally further comprise a solvent (f). The formulation may also optionally further comprise a non-ionic surfactant (g). The formulation may also optionally further comprise further formulation auxiliaries (h).

Preferably, the respective amounts of components (a) to (f) are as follows:

The amount of the at least one pesticide (a) is from 1% up to 60% by weight; preferably 5 to 50, most preferably 7.5 to 30% by weight. The amount of non-ionic surfactant (b) of formula I is from 0.5% up to 30% by weight; preferably 2 to 5% by weight. The amount of ionic tristyrylphenyl ethoxylate (c) is from 0.5% up to 30% by weight; preferably 5 to 15% by weight. The amount of oil (d) is from 5% up to 50% by weight; preferably 20 to 40% by weight. If a solvent (f) is present, the amount of solvent is from 5% up to 50% by weight preferably 20 to 40% by weight. If a non-ionic surfactant (g) is present in the formulation, the amount of non-ionic surfactant selected from the group consisting of ethyleneoxid/propyleneoxid block copolymers is from 0.5% up to 20% by weight.

Generally, the amount of water (e) add up to 100% by weight.

If a further formulation auxiliaries are present, the amount of further formulation auxiliaries is from 0.1% up to 2% by weight preferably 0.5 to 1% by weight.

Compounds of formula I are well known in the art, and described for example inter alia in WO 03/00053, WO 00/35278, WO 05/105285 and EP 1 140 741.

That the specific combination of compounds of formula I with at least one ionic tristyrylphenyl alkoxylate represents a favorable system for liquid water based agrochemical formulations not disclosed in any of these documents.

Furthermore, ethyleneoxy, which represents —CH$_2$—CH$_2$—O— is hereinbelow abbreviated as "EO" and propyleneoxy, which represents —CH$_2$—CH(CH$_3$)—O— is hereinbelow abbreviated as "PO".

In formula I, m and n represent mean values.

A preferred group of non-ionic surfactants are alcohol alkoxylates of the formula Ia $$R^1\text{—}O\text{-}(\text{-}AO\text{—})_o\text{—}H \qquad (Ia)$$

in which
$R^1$ has the meaning indicated above: and o represents numbers from 2 to 20.

A further preferred group of non-ionic surfactants are alcohol alkoxylates of the formula Ib $$R^1\text{—}O\text{-}(\text{-}EO\text{—})_n\text{—}(\text{—}PO\text{—})_m\text{—}H \qquad (Ib)$$

in which
$R^1$ has the meaning indicated above, and
m represents numbers from 1 to 10 and
n represents numbers from 1 to 10.

A further preferred group of non-ionic surfactants are alcohol alkoxylates of the formula Ic $$R^1\text{—}O\text{—}(\text{—}PO\text{—})_r\text{-}(EO\text{—})_s\text{—}H \qquad (Ic)$$

in which
$R^1$ has the meaning indicated above,
r represents numbers from 1 to 10 and
s represents numbers from 1 to 10.

A further preferred group of non-ionic surfactants are alcohol alkoxylates of the formula Id $$CH_3(CH_2)_tCH_2O(CH_2CH_2O)_u\text{—}H \qquad (Id)$$

in which
t represents numbers from 8 to 13 and
u represents numbers from 6 to 17.

In the formulae indicated beforehand $R^1$ preferably represents butyl, i-butyl, n-pentyl, i-pentyl, neopentyl, n-hexyl, i-hexyl, n-octyl, i-octyl, 2-ethyl-hexyl, nonyl, i-nonyl, decyl, n-dodecyl, i-dodecyl, lauryl, myristyl, i-tridecyl, trimethylnonyl, palnityl, stearyl or eicosyl, wherein 2 ethyl-hexyl is preferred.

Preferred are non-ionic surfactants are alcohol alkoxylates of the formula Ib and Ic, wherein $R^1$ is 2-ethyl-hexyl [$CH_3$—$CH_2$—$CH_2$—$CH_2$—$CH(C_2H_5)$—$CH_2$—].

More preferred are alcohol alkoxylates of the formula Ib-1, wherein

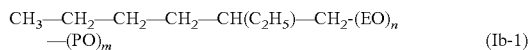

$$CH_3—CH_2—CH_2—CH_2—CH(C_2H_5)—CH_2\text{-}(EO)_n—(PO)_m \quad (Ib\text{-}1)$$

m is 1 to 5; and
n is 1 to 5;
wherein n is preferably 3 to 5, m is preferably to a value from 1 to 2; and alcohol alkoxylates of formula Ic-1

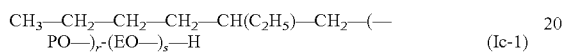

$$CH_3—CH_2—CH_2—CH_2—CH(C_2H_5)—CH_2—(\text{—}PO\text{—})_r\text{-}(EO\text{—})_s—H \quad (Ic\text{-}1)$$

r is 1 to 10, preferably 6; and
s is 1 to 10, preferably 8; and alcohol alkoxylates of formula Ic-2

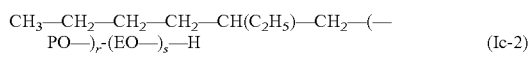

$$CH_3—CH_2—CH_2—CH_2—CH(C_2H_5)—CH_2—(\text{—}PO\text{—})_r\text{-}(EO\text{—})_s—H \quad (Ic\text{-}2)$$

r is 1 to 5, preferably 1 to 3; and
s is 1 to 5, preferably 2 to 4

Most preferred are alcohol alkoxylates of the formula Ib, wherein alcohol alkoxylates of the formula Ib-1 are utmost preferred.

As mentioned above, in all alcohol alkoxylates of formula I, the numbers given for m, n, o, r, s and u are average values (mean values).

In addition, the above formulae give a general definition of the alcohol alkoxylates. These substances are mixtures of substances of the type indicated having different chain lengths. For the indices, therefore, average values are calculated which can also differ from integers.

By way of example, an alcohol alkoxylate of the formula (Ic-1) may be mentioned, in which r represents the average value 6.2 and s represents the average value 8.3.

The ionic tristyrylphenyl alkoxylates (c) are preferably phosphated or sulfated and optionally neutralized by a base. More preferably, the tristyrylphenyl alkoxylates comprise formula II

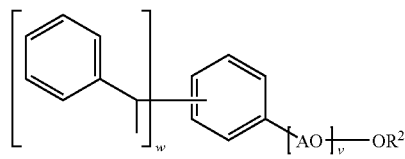

(II)

wherein w is 3, and
v is 1 to 60, more preferably 10 to 25, and most preferably 16,
[AO is EO, PO or a mixture of EO and PO moiety preferably EO; and
$R^2$ is $SO_3H$ or $H_2PO_3$.

The respective free acide forms of formula II can be also neutralized with a base e.g. an alkalimetallhydroxid (e.g. NaOH, KOH) or ammoniac or an amine (e.g. of formula III

$$NR^1R^2R^3 \quad (III)$$

wherein $R^1$, $R^2$ and $R^3$ are independently from each other hydrogen methyl, ethyl or propyl, preferably $R^1$, $R^2$ and $R^3$ are ethyl) in aqueous solution resulting in $R^2$=$SO_3X$ or $HPO_3Y$ (wherein X and Y represent independently from each other $NH_4^+$, $(NR^1R^2R^3)^+$ with $R^1$, $R^2$ and $R^3$ as defined above, $Na^+$ or $K^+$.

Most preferred are ionic tristyrylphenol ethoxylates, which are preferably phosphated or sulfated and optionally neutralized by a base, more preferably those, in which $R^2$ is $SO_3X$ and $HPO_3Y$, wherein X and Y have the meaning as defined above. Herein, the tristyrylphenyl ethoxylates of formula IIa are utmost preferred:

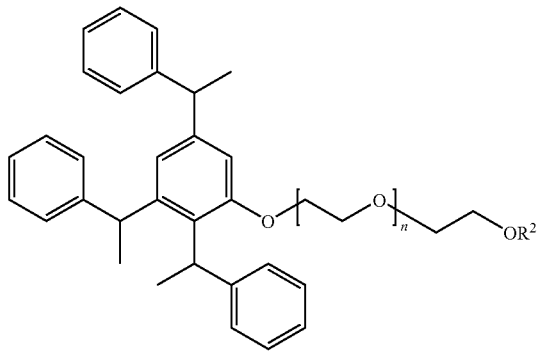

(IIa)

wherein v is 1 to 60, more preferably 10 to 25, and most preferably 14 to 18; and $R^2$ is $SO_3H$ or $H_2PO_3$.

The respective free acide forms can be also neutralized with a base e.g. an alkalimetallhydroxid (e.g. NaOH, KOH) or ammoniac or an amine (e.g. of formula III

$$NR^1R^2R^3 \quad (III)$$

wherein $R^1$, $R^2$ and $R^3$ are independently from each other hydrogen, methyl, ethyl or propyl, preferably $R^1$, $R^2$ and $R^3$ are ethyl) in aqueous solution resulting in $R^2$=$SO_3X$ or $HPO_3Y$ (wherein X and Y represent independently from each other $NH_4^+$, $(NR^1R^2R^3)^+$ with $R^1$, $R^2$ and $R^3$ as defined above, or $K^+$.

Most preferred are compounds of formula IIa, wherein $R^2$ is $SO_3X$ and $HPO_3Y$, wherein X and Y have the meaning as defined above.

The preparation of compounds of formula II and IIa is known in the art and can be performed e.g. in analogy to the methods described in U.S. Pat. No. 5,082,591. Compounds of formula II and IIa can be obtained by condensation of styrene on phenol followed by ethoxylation, or by ethoxylation-propoxylation. Anionic tristyrylphenyl alkoxylates can be prepared by phosphatation (e.g. with $P_2O_5$) or Sulfatation (e.g. with $H_2NSO_3H$) optionally followed by neutralisation with a base (e.g. alkalihydroxid or ammoniak) Compounds of formula I and/or II are available in commercial products, for example Soprophor FLK, Soprohor FL, Soprophor 4D384, Soprophor 4D360 (potassium salt, triethanolamine salt, $NH_4^+$-salt) from Rhodia.

The term "at least one oil" (d) means that either one oil or a mixture of oils can be used.

The oil (d) can be selected from the group consisting of mineral oils and synthetic oils and vegetable (plant) and animal oils, e.g. mixtures of $C_8$ to $C_{22}$ fatty acids. Examples are mineral oil fractions of medium to high boiling point, for example kerosene and diesel fuel, petroleum derivatives furthermore coal tar oils, hydrocarbons, paraffin oils, unhydrogenated, hydrogenated or partially hydrogenated aromatic or alkylaromatic compounds from the benzene or naphthalene series, fats and oils of vegetable or animal origin, such as mono-, di- and triglycerides, pure or as a mixture, for example in the form of oily extracts of natural products, for example olive oil, soybean oil, sunflower oil, castor oil, sesame oil, corn oil, groundnut oil, rapeseed oil, linseed oil, almond oil, sunflower oil, coco, palm kern, palm, soya, rapeseed, canola, maize, but also beef tallow oil, sperm oil, hering oil, castor oil and their raffinates, for example hydrogenated or partially hydrogenated products thereof in particular methyl and ethyl esters. Preferred oils are any kind of mineral oil (petroleum derivatives) but also vegetable oils like coco, palm kern, palm, soya, rapeseed, canola, maize, but also beef tallow oil, sperm oil, hering oil, castor oil, which are mixtures of natural occurring C8 to C22 fatty acids, and which may be optionally hydrogenated or partially hydrogenated products thereof in particular methyl and ethyl esters.

The term "at least one solvent" (f) means that either one organic solvent or a mixture of organic solvents can be used.

The organic solvent (f) can be either a polar or non-polar solvent. Examples of suitable solvents (f) are $C_8$ to $C_{11}$ aromatic petroleum derivatives (aromatic hydrocarbons) with a solubility in water <0.1% (w/w) and a distillation range from 130° C. to 300° C. (commercial available under the following brand names: Solvesso 100, Solvesso 150, Solvesso 200, Solvesso 150ND, solvesso 200ND, Aromatic 150, Aromatic 200, Hydrosol A 200, Hydrosol A 230/270, Caromax 20, Caromax 28, Aromat K 150, Aromat K 200, Shellsol A 150, Shellsol A 100, Fin FAS-TX 150, Fin FAS-TX 200), hydrocarbons such as aromatic depleted, linear paraffinic, isoparaffinic, cycloparaffinic having a flash point between 40° C. and 250° C. and a distillation range from 150° C. to 450° C., Anisole, Dimethylsulfoxid (DMSO), N-Methylvalerolactam and Lactones such as γ-Butyrolacton; and Esters such as Benzylacetate, Benzyl benzoate, Butyl benzoate, 2-, ethoxypropylacetate, methyl proxitol acetate; Tributyl phosphate and Amides such as N,N-dimethyl octanamide, and/or N,N-dimethyl decanamide; and Ketones such as 2-heptanone, cyclohexanone, acetophenone, and acetophenone derivatives such as 4-methoxy acetophenone; and Alcohols such as cyclohexanol, Benzylalcohol diacetone alcohol, for example 4-hydroxy-4-methyl-2-pentanone, n-octanol, 2 ethylhexanol Diesters such as mixtures of Dimethyl glutarate, dimethyl succinate and dimethyl adipate, or mixtures of Diisobutyl glutarate, diidobutyl succinate and diisobutyl adipate and glycol and derivatives such as polyethylene glycol, glycerol, propylene glycol, propylene glycol monomethyl ether acetate, dipropylene glycol monomethyl ether, propylene glycol monophenyl ether; and alkylene carbonates such as Propylencarbonate, Butylene carbonate, and pyrrolidone, derivatives such as N-octylpyrrolidone, N-ethyl pyrrolidone, N-docedyl pyrrolidone, and Lactate esters such as n-propyl lactate, methyl lactate, ethyl lactate, isopropyl lactate, butyl lactate, commercially available under the tradenames Purasolv NPL-Purasolv ML-Purasolv EL-Purasolv IPL Purasolv BL or mixtures selected from at least two of the aforementioned solvents.

As mentioned above, the liquid formulation comprises at least one oil (d) and optionally further at least one solvent (f).

According to the invention the pesticide is present in the aqueous phase in form of a suspension and the oil is essentially free of pesticide. The term "essentially" means the concentration of the pesticide in the oil is not exceeding 5 wt %, preferably 2 wt % and especially 0.5 wt %, in respect to the total weight of the oil.

In case that more than one pesticide is used, e.g. two, the pesticides could be present either in solid form (suspension in water) or solubilized in water. Herein, the pesticides can be present under the same form (e.g. both are present in solid form in form of a suspension) or under different forms (e.g. one pesticide is solubilized in water and the other is present in form of a suspension in the aqueous phase). In a particular preferred embodiment, both pesticides are present in form of a suspension in the aqueous phase, and the oil is essentially free of pesticide. Herein, it is preferred that the formulation does not comprise an organic solvent.

The formulations as defined above, may comprise a further non-ionic surfactant (g) selected from the group of ethylene propylene oxide block copolymers, wherein the molecular weight of such polymers may lay in a range from 850 g/mol to 3250 g/mol (e.g. commercial available as Pluronic® PE types from BASF (e.g. Pluronic® PE 3100, Pluronic® PE 3500, Pluronic® PE 4300, Pluronic® PE 6100, Pluronic® PE 6200, Pluronic® PE 6400, Pluronic® PE 6800, Pluronic® PE 7400, Pluronic® PE 8100, Pluronic® PE 9200, Pluronic® PE 9400, Pluronic® PE 10100, Pluronic® PE 10300, Pluronic® PE 10400, Pluronic® PE 10500).

In a particular preferred embodiment, the formulation comprises (a) one or two pesticides present in form of a suspension;
(b) at least one non-ionic surfactant of formula I, preferably Ib or Ic, more preferably Ib-1 or Ic-1 or Ic2, most preferably Ib-1
(c) at least one ionic tristyrylphenyl alkoylate, preferably of formula II, more preferably of formula II, most preferably of formula IIa; and
(d) at least one oil, wherein the oil is essentially free of pesticide; and
(e) water; and
(g) non-ionic surfactant (g) selected from the group of ethylene propylene oxide block copolymers; and no solvent(s).

Optionally, the formulation may comprise also further formulation auxiliaries (h) suitable for the formulation of agrochemicals, such as additional surfactants, antifoaming agents, anti-freezing agents, stabilizers, preservatives and/or antioxidants optionally if the formulation is intended for seed treatment purposes dyes and/or binders.

Suitable stabilizers are, for example carboxylic acids (citric acid, acetic acid, dodecylbenzensulfonic acid), orthophosphoric acid dodecylbenzensulfonic acid and suitable salts thereof. Suitable antioxidants are for example as Butylhydroxytoluene Suitable preservatives are for example 1,2-benzisothiazolin-3-one and/or 2-Methyl-2H-isothiazol-3-one or sodium benzoate or benzoic acid.

Suitable antifreeze agents are for example glycerine, ethylene glycol, hexyleneglycol and propylene glycol.

Suitable antifoaming agents are for example antifoaming agents based on modified silicon, for example PolyDiMethylSiloxanes.

Suitable binders can be added to improve the adhesion of the active materials on the seeds after treatment. Suitable binders are Polyvinylpyrrolidone, Polyvinylacetate, Polyvinylalkohol and Tylose.

Suitable dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108. They must be soluble in solvents.

The formulations are prepared in a known manner (see e.g. for review U.S. Pat. No. 3,060,084, EP-A 707 445 (for liquid concentrates), Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the pesticide with the solvent and/or mineral oil as defined above and surfactants (b), (c) and optionally (f) according to the present invention as defined above and optionally further surfactant(s) and formulation auxiliaries as defined above.

For example, the formulations can be prepared, by comminuting the corresponding pesticide(s) with addition of oil, solvent(s) as defined above under stirring till the active is fully in solution, then by adding (emulsifiers, antifreeze, antifoaming agents and lastly water) and, if appropriate, further auxiliaries like preservative of dye in a vessel. Another example for preparation is to prepare a premix wet mill-base of the pesticides/to fit with the required particle size distribution. To this wet mill base, further formulation auxiliaries are added, such as e.g antifoams and thickener. An oil and optionally an emulsifier are mixed and stirred to prepare an oily solution. The wet mill-base with formulation auxiliaries (antifoams and thickener) is mixed under stirring with the oily solution to give the final formulation.

The term "at least one pesticide" within the meaning of the invention states that one or more compounds can be selected from the group consisting of fungicides, insecticides, nematicides herbicide and/or safer or growth regulators can be used. The skilled artisan is familiar with such pesticides, which can be, for example, found in the Pesticide Manual, 13th Ed. (2003), The British Crop Protection Council, London.

The following list of pesticides together with which the compounds according to the invention can be used, is intended to illustrate possibilities, but not to impose any limitation:

The insecticide can be selected from the group consisting of

A.1. Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

A.2. Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

A.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, gamma-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

A.4. Growth regulators: a) chitin synthesis inhibitors: benzoylureas: chlorfluazuron, diflubenzuron, flucycloxuron, flufenoxuron, hexaflumuron, lufenuron, novaluron, tefluben-zuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

A.5. Nicotinic receptor agonists/antagonists compounds: clothianidin, dinotefuran, imidacloprid, thiamethoxam, nitenpyram, acetamiprid, thiacloprid; the thiazol compound of formula (I¹)

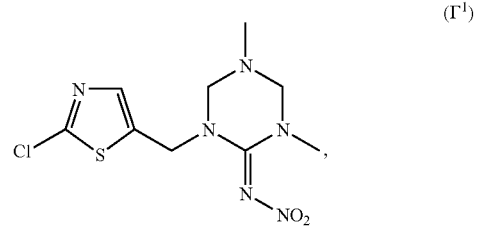

(I¹)

A.6. GABA antagonist compounds: acetoprole, endosulfan, ethiprole, fipronil, vaniliprole, pyrafluprole, pyriprole, the phenylpyrazole compound of formula I²

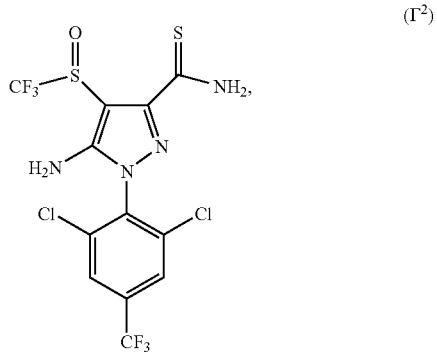

(I²)

A.7. Macrocyclic lactone insecticides: abamectin, emamectin, milbemectin, lepimectin, spinosad, the compound of formula (I³) (CAS No. 187166-40-1)

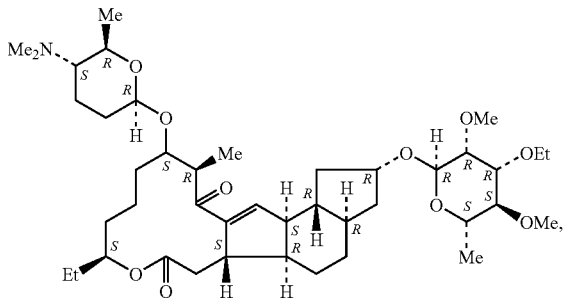

(I³)

A.8. METI I compounds: fenazaquin, pyridaben, tebufenpyrad, tolfenpyrad, flufenerim;

A.9. METI II and III compounds: acequinocyl, fluacyprim, hydramethylnon;

A.10. Uncoupler compounds: chlorfenapyr;

A.11. Oxidative phosphorylation inhibitor compounds: cyhexatin, diafenthiuron, fenbutatin oxide, propargite;

A.12. Moulting disruptor compounds: cyromazine;

A.13. Mixed Function Oxidase inhibitor compounds: piperonyl butoxide;

A.14. Sodium channel blocker compounds: indoxacarb, metaflumizone,

A.15. Various: benclothiaz, bifenazate, cartap, flonicamid, pyridalyl, pymetrozine, sulfur, thiocyclam, flubendiamide, cyenopyrafen, flupyrazofos, cyflumetofen, amidoflumet, the aminoquinazolinone compound of formula I'

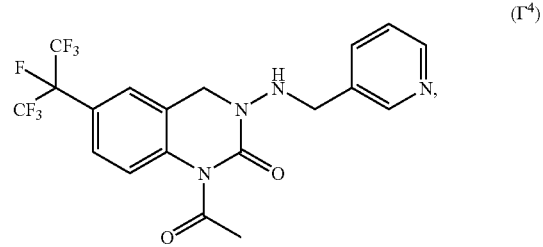

(I⁴)

N—R'-2,2-dihalo-1-R''cyclo-propanecarboxamide-2-(2,6-dichloro-α,α,α-tri-fluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R'' is hydrogen or methyl and R''' is methyl or ethyl, anthranilamide compounds of formula I⁵

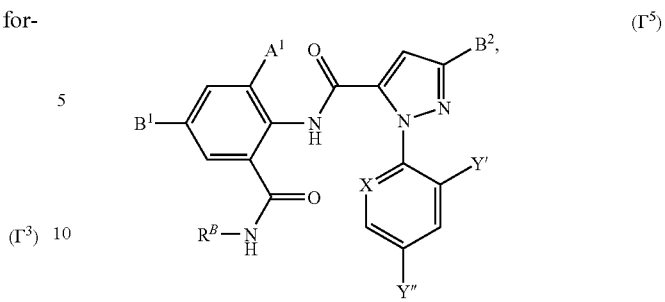

(I⁵)

wherein $A^1$ is $CH_3$, Cl, Br, I, X is C—H, C—Cl, C—F or N, Y' is F, Cl, or Br, Y'' is H, F, Cl, $CF_3$, $B^1$ is hydrogen, Cl, Br, I, CN, $B^2$ is Cl, Br, $CF_3$, $OCH_2CF_3$, $OCF_2H$, and $R^B$ is hydrogen, $CH_3$ or $CH(CH_3)_2$, and malononitrile compounds as described in JP 2002 284608, WO 02/89579, WO 02/90320, WO 02/90321, WO 04/06677, WO 04/20399, JP 2004 99597, WO 05/68423, WO 05/68432, or WO 05/63694, especially the malononitrile compounds $CF_3(CH_2)_2C(CN)_2CH_2(CF_2)_3$ $CF_2H$, $CF_3(CH_2)_2C(CN)_2CH_2(CF_2)_5CF_2H$, $CF_3(CH_2)_2C(CN)_2(CH_2)_2C(CF_3)_2F$, $CF_3(CH_2)_2C(CN)_2(CH_2)_2(CF_2)_3$ $CF_3$, $CF_2H(CF_2)_3CH_2C(CN)_2CH_2(CF_2)_3CF_2H$, $CF_3(CH_2)_2$ $C(CN)_2CH_2(CF_2)_3CF_3$, $CF_3(CF_2)_2CH_2C(CN)_2CH_2(CF_2)_3$ $CF_2H$, and $CF_3CF_2CH_2C(CN)_2CH_2(CF_2)_3CF_2H$ The commercially available compounds of the group A may be found in The Pesticide Manual, 13th Edition, British Crop Protection Council (2003) among other publications. Thioamides of formula I² and their preparation have been described in WO 98/28279. Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Cyflumetofen and its preparation have been described in WO 04/080180.

Anthranilamides of formula I⁵ and their preparation have been described in WO 01/70671; WO 02/48137; WO 03/24222, WO 03/15518, WO 04/67528; WO 04/33468; and WO 05/118552. The malononitrile compounds $CF_3(CH_2)_2C$ $(CN)_2CH_2(CF_2)_3CF_2H$, $CF_3(CH_2)_2C(CN)_2CH_2(CF_2)_5$ $CF_2H$, $CF_3(CH_2)_2C(CN)_2(CH_2)_2C(CF_3)_2F$, $CF_3(CH_2)_2C$ $(CN)_2(CH_2)_2(CF_2)_3CF_3$, $CF_2H(CF_2)_3CH_2C(CN)_2CH_2$ $(CF_2)_3$ $CF_2H$, $CF_3(CH_2)_2C(CN)_2CH_2(CF_2)_3CF_3$, $CF_3(CF_2)_2$ $CH_2C(CN)_2CH_2(CF_2)_3CF_2H$, and $CF_3CF_2CH_2C(CN)_2CH_2$ $(CF_2)_3CF_2H$ have been described in WO 05/63694.

The fungicide can be selected from the group consisting of 1. Strobilurins such as azoxystrobin, dimoxystrobin, enestroburin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]benzyl)carbamate, methyl (2-chloro-5-[1-(6-methylpyridin-2- ylmethoxyimino)ethyl]benzyl)carbamate, methyl 2-(ortho-((2,5-dimethylphenyloxymethylene)phenyl)-3-methoxyacrylate;

2. Carboxamides such as
carboxanilides: benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(2-cyanophenyl)-3,4-dichloroisothiazole-5-carboxamide;
carboxylic acid morpholides: dimethomorph, flumorph;
benzamides: flumetover, fluopicolide (picobenzamid), zoxamide;
other carboxamides: carpropamid, diclocymet, mandipropamid, N-(2-(4-[3-(4-chlorophenyl) prop-2-ynyloxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide;

3. Azoles such as
triazoles: bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole;
imidazoles: cyazofamid, imazalil, pefurazoate, prochloraz, triflumizole;
benzimidazoles: benomyl, carbendazim, fuberidazole, thiabendazole;
others: ethaboxam, etridiazole, hymexazole;

4. Nitrogenous heterocyclyl compounds such as
pyridines: fluazinam, pyrifenox, 3-[5-(4-chlorophenyl)-2,3-dimethylisoxazolidin-3-yl]-pyridine;
pyrimidines: bupirimate, cyprodinil, ferimzone, fenarimol, mepanipyrim, nuarimol, pyrimethanil;
piperazines: triforine;
pyrroles: fludioxonil, fenpiclonil;
morpholines: aldimorph, dodemorph, fenpropimorph, tridemorph;
dicarboximides: iprodione, procymidone, vinclozolin;
others: acibenzolar-S-methyl, anilazine, captan, captafol, dazomet, diclomezine, fenoxanil, folpet, fenpropidin, famoxadone, fenamidone, octhilinone, probenazole, proquinazid, pyroquilon, quinoxyfen, tricyclazole, 5-chloro-7-(4-methylpiperidin-1-yl)-6-(2,4,6-trifluorophenyl)-[1,2,4]triazolo[1,5-a]pyrimidine, 2-butoxy-6-iodo-3-propylchromen-4-one, N,N-dimethyl-3-(3-bromo-6-fluoro-2-methylindole-1-sulfonyl)-[1,2,4]triazole-1-sulfonamide;

5. Carbamates and dithiocarbamates such as
dithiocarbamates: ferbam, mancozeb, maneb, metiram, metam, propineb, thiram, zineb, ziram;
carbamates: diethofencarb, flubenthiavalicarb, iprovalicarb, propamocarb, methyl 3-(4-chlorophenyl)-3-(2-isopropoxycarbonylamino-3-methylbutyrylamino)propionate, 4-fluorophenyl N-(1-(1-(4-cyanophenyl)ethanesulfonyl)but-2-yl)carbamate;

6. Other fungicides such as
guanidines: dodine, iminoctadine, guazatine;
antibiotics: kasugamycin, polyoxins, streptomycin, validamycin A;
organometallic compounds: fentin salts;
sulfur-containing heterocyclyl compounds: isoprothiolane, dithianon;
organophosphorus compounds: edifenphos, fosetyl, fosetyl-aluminum, iprobenfos, pyrazophos, tolclofos-methyl, phosphorous acid and its salts;
organochlorine compounds: thiophanate-methyl, chlorothalonil, dichlofluanid, tolylfluanid, flusulfamide, phthalide, hexachlorbenzene, pencycuron, quintozene;
nitrophenyl derivatives: binapacryl, dinocap, dinobuton;
inorganic active compounds: Bordeaux mixture, copper acetate, copper hydroxide, copper oxychloride, basic copper sulfate, sulfur;
others: spiroxamine, cyflufenamid, cymoxanil, metrafenone.

The herbicide is selected from the group consisting of
b1) lipid biosynthesis inhibitors such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, diallate, dimepiperate, EPTC, esprocarb, ethiolate, isopolinate, methiobencarb, molinate, orbencarb, pebulate, prosulfocarb, sulfallate, thiobencarb, tiocarbazil, triallate, vernolate, benfuresate, ethofumesate and bensulide;
b2) ALS inhibitors such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac;
b3) photosynthesis inhibitors such as atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluoron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluoron, phenobenzuron, siduron, tetrafluoron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazone, propanil, pentanochlor, pyridate, and pyridafol;
b4) protoporphyrinogen-IX oxidase inhibitors such as acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen and etnipromid;

b5) bleacher herbicides such as metflurazon, norflurazon, flufenican, diflufenican, picolinafen, beflubutamid, fluridone, fluorochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethylphenoxy)-2-(4-trifluoromethylphenyl) pyrimidine, and also 3-heterocyclyl-substituted benzoyl derivatives of the formula II (see in WO 96/26202, WO 97/41116, WO 97/41117 and WO 97/41118)

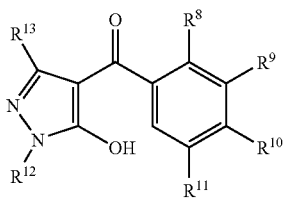

in which the variables $R^8$ to $R^{13}$ are as defined below:

$R^8$, $R^{10}$ are hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl or $C_1$-$C_6$-alkylsulfonyl;

$R^9$ is a heterocyclic radical selected from the group consisting of such as thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, where the nine radicals mentioned may be unsubstituted or mono- or polysubstituted, e.g. mono-, di-, tri- or tetrasubstituted, by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;

$R^{11}$ is hydrogen, halogen or $C_1$-$C_6$-alkyl;

$R^{12}$ is $C_1$-$C_6$-alkyl;

$R^{13}$ is hydrogen or $C_1$-$C_6$-alkyl.

b6) EPSP synthase inhibitors such as glyphosate;
b7) glutamine synthase inhibitors such as glufosinate and bilanaphos;
b8) DHP synthase inhibitors such as asulam;
b9) mitose inhibitors such as benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, tebutam, chlorthal, carbetamide, chlorbufam, chlorpropham and propham;
b10) VLCFA inhibitors such as acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamid, napropamide, naproanilide, pethoxamid, flufenacet, mefenacet, fentrazamide, anilofos, piperophos, cafenstrole, indanofan and tridiphane;
b11) cellulose biosynthesis inhibitors such as dichlobenil, chlorthiamid, isoxaben and flupoxam;
b12) decoupler herbicides such as dinofenate, dinoprop, dinosam, dinoseb, dinoterb, DNOC, etinofen and medinoterb;
b13) auxin herbicides such as clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, quinclorac, quinmerac, clopyralid, fluoroxypyr, picloram, triclopyr and benazolin;

b14) auxin transport inhibitors such as naptalam, diflufenzopyr;
b15) benzoylprop, flamprop, flamprop-M, bromobutide, chlorflurenol, cinmethylin, methyldymron, etobenzanid, fosamine, metam, pyributicarb, oxaziclomefone, dazomet, triaziflam and methyl bromide.

Fungicides and Insecticides are preferred.
Preferred Insecticides are
Carbamates such as Alanycarb, Benfuracarb, Carbaryl, Carbosulfan, Fenoxycarb, Furathiocarb, Indoxacarb, Methiocarb, Methomyl, Oxamyl, Pirimicarb, Propoxur, Thiodicarb, Triazamate;
Pyrethroids such as Bifenthrin, Cyfluthrin, Cypermethrin, alpha-Cypermethrin, Deltamethrin, Esfenvalerate, Ethofenprox, Fenpropathrin, Fenvalerate, Cyhalothrin, Lambda-Cyhalothrin, Permethrin, Silafluofen, Tau-Fluvalinate, Tefluthrin, Tralomethrin, Zeta-Cypermethrin;
Arthropod growth regulators such as
chitin synthesis inhibitors: benzoylureas: Chlorfluazuron, Diflubenzuron, Flucycloxuron, Flufenoxuron, Hexaflumuron, Lufenuron, Novaluron, Teflubenzuron, Triflumuron; Buprofezin, Diofenolan, Hexythiazox, Etoxazole, Clofentazine;
b) ecdysone antagonists: Halofenozide, Methoxyfenozide, Tebufenozide;
c) juvenoids: Pyriproxyfen, Methoprene, Fenoxycarb;
d) lipid biosynthesis inhibitors: Spirodiclofen;
Neonicotinoids such as Acetamiprid, Clothianidin, Flonicamid, Imidacloprid, Nitenpyram, Thiacloprid, Thiamethoxam, Dinetofuran
and Ethiprole, Fipronil, Metaflumizone, N—R'-2,2-dihalo-1-R''cyclo-propanecarboxamide-2-(2,6-dichloro-α,α,α-trifluoro-p-tolyl)hydrazone or N—R'-2,2-di(R''')propionamide-2-(2,6-dichloro-α,α,α-trifluoro-p-tolyl)-hydrazone, wherein $R^1$ is methyl or ethyl, halo is chloro or bromo, R'' is hydrogen or methyl and R''' is methyl or ethyl, Abamectin, Acequinocyl, Amitraz, Azadirachtin, Bifenazate, *Bacillus thuringiensis, Bacillus subtilis*, Cartap, Chlorfenapyr, Chlordimeform, Cyromazine, Diafenthiuron, Diofenolan, Emamectin, Endosulfan, Fenazaquin, Formetanate, Formetanate hydrochloride, Hydramethylnon, Indoxacarb, 4-{(2Z)-2-({[4-(trifluoro-methoxy)anilino]carbonyl}hydrazono)-2-[3-(trifluoromethyl)phenyl]ethyl}benzo-nitrile, Pyridaben, Pyridalyl, Pymetrozine, Spinosad, Sulfur, Tebufenpyrad, and Thiocyclam.

More preferred Insecticides are Fipronil, Flufenoxuron, Teflubenzuron, metaflumizone and Alphacypermethrin.
Most preferred Insecticides are Fipronil, Flufenoxuron and Alphacypermethrin.

As mentioned above, also mixtures of actives are preferred. For example, the Insecticide following mixtures are preferred: the mixture of alphacypermethrin and acetamiprid; the mixture of fipronil and imidacloprid; the mixture of fipronil and acetamiprid; the mixture of fiponil and acephate; the mixture of fipronil and thiametoxan; the mixture of fipronil and pymetrozine; the mixture of fipronil and alphacypermethrin; the mixture of metaflumizone and acetamiprid; the mixture of metaflumizone and teflubenzuron; the mixture of alphacypermethrin and chlorpyrifos; and the mixture of metaflumizone and flufenoxuron, wherein the mixture of fipronil and alphacypermethrin is most preferred.

Preferred fungicides are epoxiconazole, pyraclostrobin, kresoxim-methyl, carbendazim, metrafenone, boscalid, triticonazole, metconazole, dimethomorph, fenpropimorph, prochloraz, vinclozolin, iprodione, ditianon, metiram, tebuconazole, azoxystrobin, mancozeb, trifloxystrobin, chlorothalonil, metalaxyl, fosetyl, difemoconazole, cyprodinil, spiroxamine, prothioconazole, picoxystrobin.

All embodiments of the formulations as defined above are hereinbelow referred to as "formulation according to the present invention".

The present invention furthermore relates to a method of combating harmful insects and/or phytopathogenic fungi, which comprises contacting said harmful insects and/or phytopathogenic fungi, their habit, breeding ground, food supply, plant, seed, soil, area, material or environment in which the harmful insects and/or phytopathogenic fungi are growing or may grow, or the materials, plants, seeds, soils, surfaces or spaces to be protected from attack or infestation by said harmful insects and/or phytopathogenic fungi with an effective amount of a agrochemical formulation according to the present invention.

Thus, the formulations according to the present invention can therefore be used for the control of a multitude of phytopaghogenic fungi or insects on various cultivated plants or weeds in, such as wheat, rye, barley, oats, rice, corn, grass, bananas, cotton, soya, coffee, sugar cane, vines, fruits and ornamental plants, and vegetables, such as cucumbers, beans, tomatoes, potatoes and cucurbits, and on the seeds of these plants.

The present invention furthermore relates to a method of controlling undesired vegetation and/or a method of growth regulation of plants, which comprises allowing a herbicidally or growth regulatory effective amount of a agrochemical formulation according to the present invention to act on plants, their habitat or on seed of said plants.

The term phytopathogenic fungi includes but is not limited to the following species:

*Alternaria* spp. on rice, vegetables, soybeans, canola/oilseed rape and sugarbeet and fruit, *Aphanomyces* spp. on sugarbeet and vegetables *Bipolaris* and *Drechslera* spp. on corn, cereals, rice and turf, *Blumeria graminis* (powdery mildew) on cereals, *Botrytis cinerea* (gray mold) on strawberries, vegetables, ornamentals and grapevines, *Bremia lactucae* on lettuce *Cercospora* spp. on corn, soyabeans and sugarbeet *Cochliobolus* spp. on corn, cereals on rice (e.g. *Cochliobolus sativus* on cereals, *Cochliobolus miyabeanus* on rice) *Colletotrichum* spp. on soybeans and cotton *Drechslera* spp. on cereals and corn *Exserohilum* spp. on corn *Erysiphe cichoracearum* and *Sphaerotheca fuliginea* on cucurbits, *Erysiphe necator* on grapevines *Fusarium* and *Verticillium* spp. on various plants, *Gaeumannomyces graminis* on cereals *Gibberella* spp. on cereals and rice (e.g. *Gibberella fujikuroi* on rice, *Gibberella zeae* on cereals) Grainstaining complex on rice *Microdochium nivale* on cereals *Mycosphaerella* spp. on cereals, bananas and peanuts, *Phakopsora pachyrhizi* and *Phakopsora meibomiae* on soybeans *Phomopsis* spp. on soybeans and sunflower *Phytophthora infestans* on potatoes and tomatoes, *Plasmopara viticola* on grapevines, *Podosphaera leucotricha* on apples, *Pseudocercosporella herpotrichoides* on wheat and barley, *Pseudoperonospora* spp. on hops and cucumbers, *Puccinia* spp. on cereals and corn, *Pyrenophora* spp. on cereals *Pyricularia oryzae* on rice, *Cochliobolus miyabeanus* and *Corticium sasakii* (*Rhizoctonia solani*), *Fusarium semitectum* (and/or moniliforme), *Cercospora oryzae*, *Sarocladium oryzae*, *S. attenuatum*, *Entyloma oryzae*, *Gibberella fujikuroi* (bakanae), Grainstaining complex (various pathogens), *Bipolaris* spp., *Drechslera* spp. and *Pythium* and *Rhizoctonia* spp. on rice, corn, cotton, canola, oilseed rape, sunflower, sugarbeet, vegetables, turf, nuts and other various plants *Rhizoctonia solani* on potato *Sclerotinia* spp. on canola/oilseed rape and sunflower *Septoria tritici* and *Stagonospora nodorum* on wheat, *Uncinula necator* on grapevines, *Sphacelotheca reiliana* on corn *Thievaliopsis* spp. on soybeans and cotton *Tilletia* spp. on cereals *Ustilago* spp. on cereals corn, and sugar cane, and *Venturia* spp. (scab) on apples and pears;

The term harmful insect pests includes but is not limited to the following arthropods and nematodes:

millipedes (Diplopoda) such as *Blaniulus* species

Ants (Hymenoptera), such as. *Atta capiguara, Atta cephalotes, Atta laevigata, Atta robusta, Atta sexdens, Atta texana, Monomorium pharaonis, Solenopsis geminata, Solenopsis invicta, Pogonomyrmex* species and *Pheidole megacephala,*

Beetles (Coleoptera), such as *Agrilus sinuatus, Agriotes lineatus, Agriotes obscurus* and other *Agriotes* species, *Amphimallus solstitialis, Anisandrus dispar, Anthonomus grandis, Anthonomus pomorum, Aracanthus morei, Atomaria linearis, Blapstinus* species, *Blastophagus piniperda, Blitophaga undata, Bothynoderes punciventris, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus* and other *Conoderus* species, *Conorhynchus mendicus, Crioceris asparagi, Cylindrocopturus adspersus, Diabrotica (longicornis) barberi, Diabrotica semi-punctata, Diabrotica speciosa, Diabrotica undecimpunctata, Diabrotica virgifera* and other *Diabrotica* species, *Eleodes* species, *Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus* and other *Limonius* species, *Lissorhoptrus oryzophilus, Listronotus bonariensis, Melanotus communis* and other *Melanotus* species, *Meligethes aeneus, Melolontha hippocastani, Melolontha melolontha, Oulema oryzae, Ortiorrhynchus sulcatus, Oryzophagus oryzae, Otiorrhynchus ovatus, Oulema oryzae, Phaedon cochleariae, Phyllotreta chrysocephala, Phyllophaga cuyabana* and other *Phyllophaga* species, *Phyllopertha horticola, Phyllotreta nemorum, Phyllotreta striolata*, and other *Phyllotreta* species, *Popillia japonica, Promecops carinicollis, Premnotrypes voraz, Psylliodes* species, *Sitona lineatus, Sitophilus granaria, Sternechus pinguis, Sternechus subsignatus*, and *Tanymechus palliatus* and other *Tanymechus* species, Flies (Diptera) such as *Agromyza oryzea, Chrysomya bezziana, Chrysomya hominivorax, Chrysomya macellaria, Contarinia sorghicola, Cordylobia anthropophaga, Dacus cucurbitae, Dacus oleae, Dasineura brassicae, Delia antique, Delia coarctata, Delia platura, Delia radicum, Fannia canicularis, Gasterophilus intestinalis, Geomyza Tripunctata, Glossina morsitans, Haematobia irritans, Haplodiplosis equestris, Hypoderma lineata, Liriomyza sativae, Liriomyza trifolii, Lucilia caprina, Lucilia cuprina, Lucilia sericata, Lycoria pectoralis, Mayetiola destructor, Muscina stabulans, Oestrus ovis, Opomyza florum, Oscinella frit, Pegomya hysocyami, Phorbia antiqua, Phorbia brassicae, Phorbia coarctata, Progonya leyoscianii, Psila rosae, Rhagoletis cerasi, Rhagoletis pomonella, Tabanus bovinus, Tetanops myopaeformis, Tipula oleracea* and *Tipula paludosa,*

Heteropterans (Heteroptera), such as *Acrosternum hilare, Blissus leucopterus, Cicadellidae* such as *Empoasca fabae, Chrysomelidae, Cyrtopeltis notatus, Delpahcidae, Dysdercus cingulatus, Dysdercus intermedius, Eurygaster integriceps, Euschistus impictiventris, Leptoglossus phyllopus, Lygus lineolaris, Lygus pratensis, Nephotettix* species, *Nezara viridula, Pentatomidae, Piesma quadrata, Solubea insularis* and *Thyanta perditor,*

Aphids and other homopterans (Homoptera), e.g. *Acyrthosiphon onobrychis, Adelges laricis, Aphidula nasturtii, Aphis* fabae, Aphis forbesi, Aphis glycines, Aphis gossypii, Aphis grossulariae, Aphis pomi, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes (Myzus) persicae, Myzus ascalonicus, Myzus cerasi, Myzus varians, Nasonovia ribis-nigri, Nilaparvata lugens, Pemphigus bursarius, Pemphigus populivenae, and other Pemphigus species, Perkinsiella saccharicida, Phorodon humuli, Psyllidae such as Psylla mali, Psylla piri and other Psylla species, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, and Viteus vitifolii; Lepidopterans (Lepidoptera), for example Agrotis ypsilon, Agrotis segetum and other Agrotis species, Alabama argillacea, Anticarsia gemmatalis, Argyresthia conjugella, Autographa gamma, Bupalus piniarius, Cacoecia murinana, Capua reticulana, Chematobia brumata, Chilo suppresalis and other Chilo species, Choristoneura fumiferana, Choristoneura occidentalis, Cirphis unipuncta, Cnaphlocrocis medinalis, Cydia pomonella, Dendrolimus pini, Diaphania nitidalis, Diatraea grandiosella, Earias insulana, Elasmopalpus lignosellus, Eupoecilia ambiguella, Euxoa species, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Lerodea eufala, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Momphidae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sesamia nonagrioides and other Sesamia species, Sitotroga cerealella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis, orthopterans (Orthoptera), such as Acrididae, Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus;

termites (Isoptera), such as Calotermes flavicollis, Coptotermes species, Dalbulus maidis, Leucotermes flavipes, Macrotermes gilvus, Reticulitermes lucifugus and Termes natalensis;

thrips (Thysanoptera) such as Frankliniella fusca, Frankliniella occidentalis, Frankliniella tritici and other Frankliniella species, Scirtothrips citri, Thrips oryzae, Thrips palmi, Thrips simplex and Thrips tabaci, Arachnoidea, such as arachnids (Acarina), for example e.g. of the families Argasidae, Ixodidae and Sarcoptidae, such as Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei, and Eriophyidae species such as Aculus schlechtendali, Phyllocoptrata oleivora and Eriophyes sheldoni; Tarsonemidae species such as Phytonemus pallidus and Polyphagotarsonemus latus; Tenuipalpidae species such as Brevipalpus phoenicis; Tetranychidae species such as Tetranychus cinnabarinus, Tetranychus kanzawai, Tetranychus pacificus, Tetranychus telarius and Tetranychus urticae, Panonychus ulmi, Panonychus citri, and Oligonychus pratensis;

Nematodes, especially plant parasitic nematodes such as root knot nematodes, Meloidogyne hapla, Meloidogyne incognita, Meloidogyne javanica, and other Meloidogyne species; cyst-forming nematodes, Globodera rostochiensis and other Globodera species; Heterodera avenae, Heterodera glycines, Heterodera schachtii, Heterodera trifolii, and other Heterodera species; Seed gall nematodes, Anguina species; Stem and foliar nematodes, Aphelenchoides species; Sting nematodes, Belonolaimus longicaudatus and other Belonolaimus species; Pine nematodes, Bursaphelenchus xylophilus and other Bursaphelenchus species; Ring nematodes, Criconema species, Criconemella species, Criconemoides species, Mesocriconema species; Stem and bulb nematodes, Ditylenchus destructor, Ditylenchus dipsaci and other Ditylenchus species; Awl nematodes, Dolichodorus species; Spiral nematodes, Heliocotylenchus multicinctus and other Helicotylenchus species; Sheath and sheathoid nematodes, Hemicycliophora species and Hemicriconemoides species; Hirshmanniella species; Lance nematodes, Hoploaimus species; false rootknot nematodes, Nacobbus species; Needle nematodes, Longidorus elongatus and other Longidorus species; Lesion nematodes, Pratylenchus neglectus, Pratylenchus penetrans, Pratylenchus curvitatus, Pratylenchus goodeyi and other Pratylenchus species; Burrowing nematodes, Radopholus similis and other Radopholus species; Reniform nematodes, Rotylenchus robustus and other Rotylenchus species; Scutellonema species; Stubby root nematodes, Trichodorus primitivus and other Trichodorus species, Paratrichodorus species; Stunt nematodes, Tylenchorhynchus claytoni, Tylenchorhynchus dubius and other Tylenchorhynchus species; Citrus nematodes, Tylenchulus species; Dagger nematodes, Xiphinema species; and other plant parasitic nematode species.

The control of undesired vegetation is understood as meaning the destruction of weeds. Weeds, in the broadest sense, are understood as meaning all those plants which grow in locations where they are undesired.

As mentioned above, in one embodiment of the methods of combating harmful fungi and/or insects, the formulation according to the invention can be used also for the treatment of seeds from plants.

The present invention also comprises seeds coated with formulation according to the present invention.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

In addition, the formulation according to the invention may also be used for the treatment seeds from plants, which tolerate the action of herbicides or fungicides or insecticides owing to breeding, including genetic engineering methods, for example seeds of transgenic crops which are resistant to herbicides from the group consisting of the sulfonylureas (EP-A-0257993, U.S. Pat. No. 5,013,659), imidazolinones (see for example U.S. Pat. No. 6,222,100, WO0182685, WO0026390, WO9741218, WO9802526, WO9802527, WO 04/106529, WO 05/20673, WO 03/14357, WO 03/13225, WO 03/14356, WO 04/16073), glufosinate-type (see for example EP-A-0242236, EP-A-242246) or glyphosate-type (see for example WO 92/00377) or in seeds of plants resistant towards herbicides selected from the group of cyclohexadienone/Aryloxyphenoxypropionic acid herbicides (U.S. Pat. No. 5,162,602, U.S. Pat. No. 5,290,696, U.S. Pat. No. 5,498,544, U.S. Pat. No. 5,428,001, U.S. Pat. No. 6,069,298, U.S. Pat. No. 6,268,550, U.S. Pat. No. 6,146,867, U.S. Pat. No. 6,222,099, U.S. Pat. No. 6,414,222) or in seeds of transgenic crop plants, for example cotton, with the capability of producing Bacillus thuringiensis toxins (Bt toxins) which make the plants resistant to certain pests (EP-A-0142924, EP-A-0193259)

The seed treatment application of the formulation according to the invention is carried out by spraying or dusting the seeds before sowing of the plants and before emergence of the plants by methods known to the skilled artisan.

In the treatment of seeds the corresponding formulations are applied by treating the seeds with an effective amount of the formulation according to the present invention. Herein, the application rates of pesticide are generally from 0.1 g to 10 kg per 100 kg of seed, preferably from 1 g to 5 kg per 100 kg of seed, in particular from 1 g to 2.5 kg per 100 kg of seed. For specific crops such as lettuce or onion, the rate can be higher. The present invention provides several advantages over known agrochemical formulations: One or even more than one pesticide can be kept in stable suspension. Additionally, an oil can be added to the formulation. Furthermore, the toxicity of formulation is lowered by reducing the concentration of organic solvents compared to emulsifiable concentrates or by reducing the amount of pesticide, which is dissolved in organic solvent. A further advantage is that there is no risk of crystallization of pesticides in the emulsion phase at lower temperature or during storage, because the oil is essentially free of pesticide.

The invention is further illustrated but not limited by the following examples.

EXAMPLE 1

Preparation of a Formulation Comprising Alpha-Cypermethrin and Fipronil

A) Preparation of the premix

A solution of 280 g water, 0.75 g citric acid, 2 g Acticide MBS (1,2-Benzisothiazol-3(2H)-on+2-Methyl-2H-isothiazol-3-on), 83.3 g Pluronic PE 10500 (non-ionic surfactant, ethylene propylene oxide block copolymer from BASF, 18 wt % in water) and 100 g of Soprophor FLK (ionic trisytrylphenylethoxylate from Rhodia), were prepared by stirring in a vessel (until dissolved). Afterwards, 180 g fipronil and then 120 g alpha-cypermethrin were added under stirring conditions. Then 2.5 g Rhodorsil 416 (dialkylpolysiloxane antifoaming agent, from Rhodia) and 0.5 g Rhodorsil 432 (dialkylpolysiloxane antifoaming agent, from Rhodia) were added until the resulting mixture was homogeneous.

The resulting suspension was then passed through a horizontal bead mill (glass or zirconium beads) until a particle size specification (80%<2 microns) was achieved. After milling, 0.75 g xanthan gum (thickener) was added under stirring conditions and stirred until dissolved.

B) Preparation of the Oil Phase

In a separate vessel, 300 g corn oil and 20 g of an alcohol alkoxylate of formula (Ib) (GT2624 from AKZO) were mixed with a stirrer until a clear liquid is achieved.

C) Preparation of the Final Product 320 g of the oil-phase phase was added to 770.75 g milled premix (amount depends on purity of the particular ingredients) and blended by a colloid mill until it was homogeneous.

COMPARATIVE EXAMPLE

The procedure of Example 1 was repeated, wherein the alcohol alkoxylate of formula (Ib) in step B) was substituted by a commercial mixture of fatty acid polyethylene glycol esters (Geronol® VO 2001, a nonionic emulsifier from Rodhia) or by polyethylenglykol 300 ester of 9-octadecenoic acid (Alkamuls® A, a nonionic emulsifier from Rodhia). In both cases the formulation was not stable and separated.

The invention claimed is:

1. A formulation comprising
    (a) at least one pesticide in an amount from 1% to 60% by weight of the formulation; and
    (b) at least one non-ionic surfactant of formula I $$R^1\text{---}O\text{-}(AO)_x\text{---}(H) \tag{I}$$

wherein
    $R^1$ represents straight-chain or branched alkyl having 4 to 20 carbon atoms;
    AO is a mixture of ethyleneoxy and propyleneoxy; and
    x correspond to values from 2 to 30; and
    (c) at least one ionic tristyrylphenyl alkoxylate; and
    (d) at least one vegetable oil in an amount from 5% to 50% by weight of the formulation;
    (e) optionally, other formulation additives; and
    (f) water in an amount adding up to 100% by weight,
wherein the pesticide is present in the aqueous phase in form of a suspension and the amount of pesticide in the vegetable oil does not exceed 0.5% by weight with respect to the total weight of the vegetable oil.

2. The formulation of claim 1, additionally comprising at least one solvent (g).

3. The formulation of claim 1, wherein the non-ionic surfactant (b) comprises formula (Ib)

$$R^1\text{---}O\text{-}(A)_n\text{-}(B)_m\text{---}(H) \tag{Ib}$$

wherein
    $R^1$ represents straight-chain or branched alkyl having 4 to 20 carbon atoms;
    A is ethyleneoxy;
    B is propyleneoxy;
    and n, m correspond to values from 1 to 10 provided that the sum of m, n is at least 2.

4. The formulation of claim 3, wherein $R^1$ represents 2-ethylhexyl.

5. The formulation of claim 1, wherein component (c) represents an ionic phosphated or sulfated ionic tristyrylphenol ethoxylate.

6. The formulation of claim 1, additionally comprising a further non-ionic surfactant (g) comprising an ethyleneoxide/propyleneoxide block copolymer.

7. The formulation of claim 1, wherein the oil is free of pesticide.

8. A method of combating harmful insects and/or phytopathogenic fungi, which comprises contacting said harmful insects and/or phytopathogenic fungi, their habit, breeding ground, food supply, plant, seed, soil, area, material or environment in which the harmful insects and/or phytopathogenic fungi are growing or may grow, or the materials, plants, seeds, soils, surfaces or spaces to be protected from attack or infestation by said harmful insects and/or phytopathogenic fungi with an effective amount of a agrochemical formulation of claim 1.

9. A method of controlling undesired vegetation, comprising contacting a herbicidally effective amount of the agrochemical formulation of claim 1 with plants, their habitat or a seed of said plants.

10. A seed treated with the formulation of claim 1.

11. The formulation of claim 1, wherein the vegetable oil is selected from the group consisting of coco, palm kern, palm, soya, rapeseed, canola, maize, which are mixtures of naturally occurring C8 to C22 fatty acids, and wherein the vegetable oil is optionally hydrogenated or partially hydrogenated.

12. The formulation of claim 1, wherein the pesticide comprises at least one of fipronil or alpha-cypermethrin.

13. The formulation of claim 1, wherein the formulation is free of an organic solvent.

\* \* \* \* \*